(12) United States Patent
Zabaleta Rekondo et al.

(10) Patent No.: US 10,398,339 B2
(45) Date of Patent: Sep. 3, 2019

(54) DEVICE FOR ASSESSMENT, PREVENTION AND TREATMENT OF LOW BACK PAIN BASED ON POSTURAL RE-EDUCATION

(71) Applicant: FUNDACIÓN TECNALIA RESEARCH & INNOVATION, Donostia-San Sebastián (ES)

(72) Inventors: Haritz Zabaleta Rekondo, Donostia-San Sebastián (ES); Cristina Rodríguez De Pablo, Donostia-San Sebastián (ES)

(73) Assignee: FUNDACIÓN TECNALIA RESEARCH & INNOVATION, Donostia-San Sebastián (ES)

( * ) Notice: Subject to any disclaimer, the term of this patent is extended or adjusted under 35 U.S.C. 154(b) by 1001 days.

(21) Appl. No.: 14/779,270

(22) PCT Filed: Mar. 22, 2013

(86) PCT No.: PCT/ES2013/070188
§ 371 (c)(1),
(2) Date: Sep. 22, 2015

(87) PCT Pub. No.: WO2014/147263
PCT Pub. Date: Sep. 25, 2014

(65) Prior Publication Data
US 2016/0051182 A1    Feb. 25, 2016

(51) Int. Cl.
*A61B 5/04* (2006.01)
*A61B 5/0488* (2006.01)
(Continued)

(52) U.S. Cl.
CPC .......... *A61B 5/0488* (2013.01); *A61B 5/0051* (2013.01); *A61B 5/0053* (2013.01);
(Continued)

(58) Field of Classification Search
CPC . A61B 5/0408; A61B 5/04085; A61B 5/0416; A61B 5/0488; A61B 5/6831;
(Continued)

(56) References Cited

U.S. PATENT DOCUMENTS

| 8,092,355 B2 * | 1/2012 | Mortimer | A63B 24/00 482/1 |
| 9,392,953 B1 * | 7/2016 | Gharib | A61B 5/0488 |

(Continued)

FOREIGN PATENT DOCUMENTS

EP    2 241 245    10/2010

OTHER PUBLICATIONS

Zheng,Y., Morell, J. A Vibrotactile Feedback Approach to Posture Guidance, 2010, IEEE Haptic Symposium, pp. 315-358 (Year: 2010).*

(Continued)

*Primary Examiner* — Eun Hwa Kim

(57) ABSTRACT

Device (1) for assessing, preventing and treating LBP, which comprises:
  six units (100a, 100b, 100c, 100d, 100e, 100f), each unit comprising:
    an EMG acquisition subsystem (30a);
    connecting means (10a-20a, 10b-20b, 10c-20c, 10d-20d, 10e-20e, 10f-200 for connecting the EMG acquisition subsystem (30a) to a pair of electrodes attached to a patient's skin, such that each unit receives the surface EMG signals of a specific muscle group of the patient; and,
    a actuator (60a) for providing haptic stimulus to said muscle group;
  a muscular activity pattern recognition and feedback subsystem (200, 500);
the device further comprising:
(Continued)

a wearable garment (300, 301, 302) with a central portion (300e) to which the second and fifth units (100b, 100e) are attached parallel to each other; and a set of four straps (300a, 300b, 300c, 300d) to which ends are attached the first, third, fourth and sixth units (100a, 100c, 100d, 100f) at 45°, 135°, −135° and −45°, respectively, with respect to the second and fifth units (100b, 100e).

9 Claims, 3 Drawing Sheets

(51) Int. Cl.
*A61B 5/00* (2006.01)
*A61B 5/0408* (2006.01)
*A61B 5/0492* (2006.01)
(52) U.S. Cl.
CPC ........ *A61B 5/0057* (2013.01); *A61B 5/04017* (2013.01); *A61B 5/04085* (2013.01); *A61B 5/0492* (2013.01); *A61B 5/483* (2013.01); *A61B 5/486* (2013.01); *A61B 5/6804* (2013.01); *A61B 5/6831* (2013.01); *A61B 5/7264* (2013.01)
(58) Field of Classification Search
CPC . A61B 5/0492; A61B 5/0057; A61B 5/04017; A61B 5/486; A61B 5/6804; A61B 5/0051; A61B 5/7264
See application file for complete search history.

(56) References Cited

U.S. PATENT DOCUMENTS

2010/0217100 A1* 8/2010 LeBoeuf ................. G06F 19/00 600/382
2010/0324457 A1* 12/2010 Bean ..................... A61B 5/1116 600/595

OTHER PUBLICATIONS

Jones et al., "Biosignal and Context Monitoring: Distributed Multimedia Applications of Body Area Networks in Healthcare", Oct. 8, 2008, IEEE 10th Workshop, 6 pages.

* cited by examiner

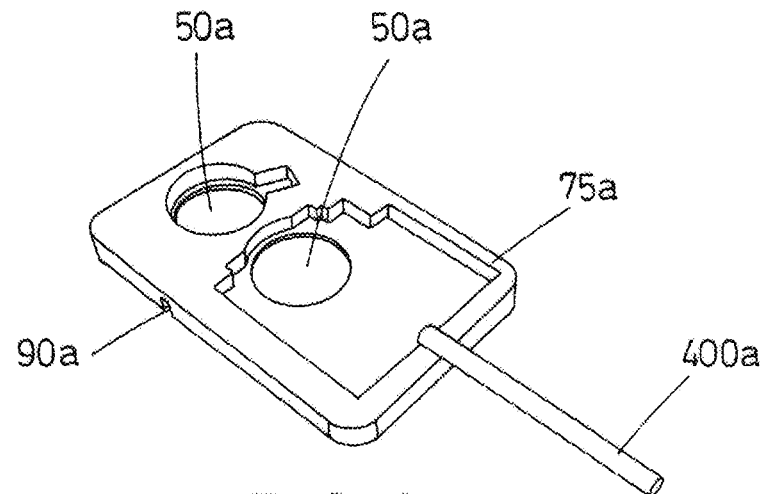
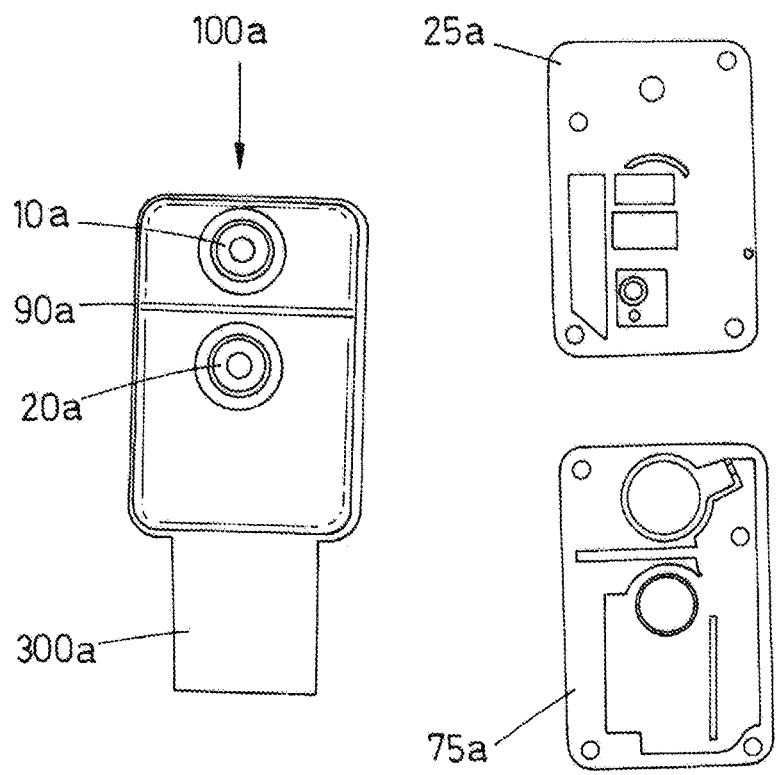

DEVICE FOR ASSESSMENT, PREVENTION AND TREATMENT OF LOW BACK PAIN BASED ON POSTURAL RE-EDUCATION

TECHNICAL FIELD

The present invention refers to low back pain assessment, treatment and prevention devices, for use in postural re-education based methods.

STATE OF THE ART

The incidence of low back pain (LBP) has been reported to be second only to that of the common cold, and in the population at large, there is an 80% chance that a person will seek medical care for a LBP disorder prior to age 55.

In addition, as stated in "*Detección de malas posturas basada en electromiografía para la prevención de lumbalgia*" (Zabaleta H. et al, $30^{th}$ Spanish Biomedical Engineering Society Annual Congress, Navarra, Spain, 2012), it is estimated that each year 50% of active workers suffer an episode of this condition and that, some time during their lives 80% of population will suffer at least one acute episode thereof. LBP consumes health care resources: medical appointments, supplementary examinations, prescriptions, etc. as well as socio economic resources, due to sick leaves. 11.4% of all sick leaves processed during 1997 in Spain were caused by low back pain, which imply an annual expense of 55.1 million € for financial assistances.

Biofeedback is used by an individual to learn how to change physiological activity for the purposes of improving health and performance by feeding back information about some of their physiological signals. It has proven useful in many fields such as balance control, sport performance, improving mobility tasks, mental relaxation, coordination tasks, as well as for the treatment of LBP. U.S. Pat. No. 5,086,779-A describes a device designed for the assessment of muscular function in cases of LBP; mainly, to corroborate claims of lumbalgia. It is based on the monitoring of an electromyogram (EMG) signal median frequency (MF). Six active surface EMG electrodes are placed bilaterally over sites at L1, L2, and L5 levels of the lower back corresponding to the longissimus thoraces, iliocostales lumborum, and multifidus muscles. Afterwards, linear regression analysis is performed on the MF parameter (obtained from the spectral analysis of the EMG signals) at all force levels and classification based on Fisher Z score is carried on for assessment. However, this system is only useful to a physician, not to the patient himself.

Information fed back to the patient by state of the art biofeedback devices are stimuli of visual and/or acoustical nature.

Biofeedback has also been used in teaching sports, as described for example in U.S. Pat. No. 8,036,849-B2. Here, a device is provided with a biofeedback module for measuring physical attributes linked to exercise, comprising: a pad that is attachable or wearable to the body of a person, a signal sensing unit installed on the pad to sense at least one type of physical attributes signal that changes according to motions of the body, and a transmitting unit for the signal. This system however, is only useful for evaluating whether a subject has a correct posture while practicing sports and is not suitable for treating patients with lumbalgia.

If biofeedback is used for alerting purposes and it is delivered for too long or too frequently, the awareness of the feedback can get lower because of a problem of habituation. It is a basic process of learning evident in a decrement in neuronal/behavioral responses to repeated sensory stimulation (Carsten M. Klingner et al, "*Habituation within the somatosensory processing hierarchy*", Behavioural Brain Research, Volume 225, Issue 2, 1 Dec. 2011, Pages 432-436, ISSN 0166-4328). The brain ignores the feedback, as it stops processing sensorial signals associated to those stimuli.

The effect of habituation can be avoided by controlling the stimulation strategy in order to significantly increase the detection of a stimulus, (Wentink E. C. et al, "*Vibrotactile stimulation of the upper leg: Effects of location, stimulation method and habituation*", $33^{rd}$ Annual International IEEE EMBS Conference, 30 Aug. 3-Sep. 2011, Boston, USA). Therefore, it is of key importance that the feedback system has a full control on the amplitude, timing and location where the feedback is provided.

Postural re-education, as used in the present specification, is a particular biofeedback technique in which the information taken from the patient is the activity of certain group of muscles. Said information is used to determine the actual activity pattern and compared to a normality pattern. Biofeedback stimuli are sent to the patient in order to advise them that a posture correction exercise should be performed. Recently published studies show that postural re-education is also effective against LBP, for example "Effectiveness of a global postural re-education program for persistent low back pain: a non-randomized controlled trial" (Bonetti F. et al, I. BMC Musculoskelet Disord, 16 Dec. 2010; 11:285).

The muscular activity pattern can also be used to perform therapeutic exercises. If these exercises are not performed in the correct way, or certain levels of activity, balance/unbalance between muscular groups are not achieved, biofeedback stimuli are sent to the patient.

DESCRIPTION OF THE INVENTION

The present invention refers to a device for the assessment, prevention and treatment of low back pain according to claim 1. Preferred embodiments of the device are defined in the dependent claims.

A first aspect of the invention relates to a device for the assessment, prevention and treatment of low back pain, which comprises:
  a first, a second, a third, a fourth, a fifth and a sixth units, each unit comprising:
    an EMG acquisition subsystem for measuring the surface electromyography, EMG, signals of a specific muscle group of a patient;
    connecting means for connecting the EMG acquisition subsystem to a pair of electrodes attached to the skin of the patient, such that each unit receives the surface electromyography, EMG, signals of a specific muscle group of the patient; and,
    an actuator for providing haptic stimulus to said muscle group of the patient;
  at least one muscular activity pattern recognition and feedback generation subsystem for:
    capturing, amplifying, filtering and sending said surface EMG signals;
    extracting certain features—such as mean frequency, RMS, mean amplitude—of said surface EMG signals;
    interpreting said surface EMG signals and determining a muscular activity pattern based on the extracted features;
    deciding whether a correction of the muscular activity pattern is needed; and, if correction is needed, activating the corresponding actuators.

The device further comprises:
a wearable garment comprising:
a central portion to which the second and fifth units are attached parallel to each other; and
a set of four straps to which the first, third, fourth and sixth units are attached; the straps have an adjustable length and being arranged relative to each other such that, upon connecting the device to each pair of electrodes:
the fourth unit is set at a position between 40° and 50° with respect to the second and fifth units;
the first unit is set at a position between 130° and 140° with respect to the second and fifth units;
the third unit is set at a position between −130° and −140° with respect to the second and fifth units;
the sixth unit is set at a position between −40° and −50° with respect to the second and fifth units.

The particular positioning of the units in the device of the invention is such that, once the device is worn by the patient, each EMG acquisition subsystem in each unit runs parallel to the direction of the muscular fibres of the relevant muscular groups, resulting in a very accurate placement of each unit.

The device of the invention, with its distributed design, can be advantageously simple in construction, thereby reducing costs. It can also be made very thin, so that performing any exercise is feasible, even in a supine position.

The haptic stimuli provided by the present invention are not interfered by external factors neither are felt by any other person but the user (contrary to acoustical biofeedback provided by some known appliances).

The device of the invention is also versatile, since allows the patient to perform posture correction exercises without steering to a screen to receive biofeedback, as occurs with visual prior art appliances. In addition, the user can keep doing their daily activities, including working.

According to a preferred embodiment, the actuators can provide haptic stimuli that can be one or more of: skin stretching, temperature change, vibration, simple touch (non vibratory), pinching of skin hair and electrical stimulation. The haptic stimuli can be either mono-modal or multimodal haptic stimuli of different nature. When the haptic stimuli provided are multimodal or have a random nature (in timing and/or amplitude), the problem of habituation is advantageously avoided.

In a preferred embodiment the actuator is a vibration actuator.

The classifying algorithm used by the muscular activity pattern recognition and feedback generation subsystem can be based on threshold approach or machine learning, and can be implemented in a microprocessor provided in the muscular activity pattern recognition and feedback generation subsystem.

The muscular activity pattern recognition and feedback generation subsystem can be also attached to the wearable garment.

Alternatively, the device may further comprise a remote control unit attached to the wearable garment for enabling communication between the units and the muscular activity pattern recognition and feedback generation subsystem, this muscular activity pattern recognition and feedback generation subsystem being a separate item from the wearable garment.

The wearable item can be a one-piece item, or a multiple-piece item.

Additional advantages and features of the invention will become apparent from the detailed description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures:

FIG. 6 shows one side of the casing.

FIG. 7 shows a front view of the first unit, together with its casing, disassembled.

DESCRIPTION OF A PREFERRED EMBODIMENT

The following description is not to be taken in a limiting sense but is given solely for the purpose of describing the broad principles of the invention. Next embodiments of the invention will be described by way of example, with reference to the above-mentioned drawings showing elements and results according to the invention.

Referring to the Figures, a preferred embodiment of the device for the assessment, prevention and treatment of low back pain, LBP, of the invention is described below.

Figure 1:
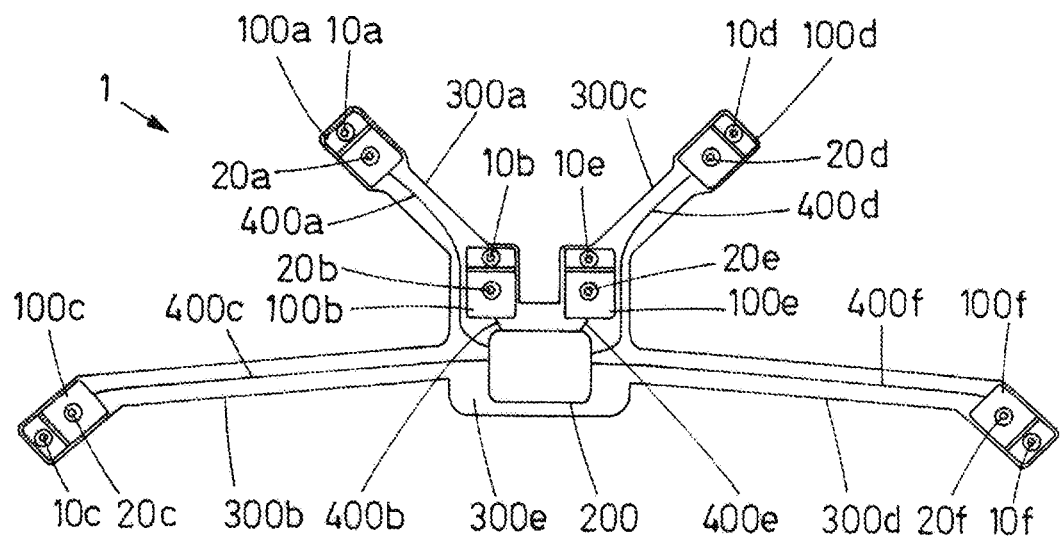
FIG. 1 shows a fist preferred embodiment of the device of the invention.

As shown in FIG. 1, a preferred embodiment of device 1 of the invention includes six units 100a, 100b, 100c, 100d, 100e, 100f connected by cables 400a, 400b, 400c, 400d to a muscular activity pattern recognition and feedback generation subsystem 200.

The six units 100a, 100b, 100c, 100d, 100e, 100f and the muscular activity pattern recognition and feedback generation subsystem 200 are attached to a belt 300 or harness made of a textile or fabric. The cables 400a, 400b, 400c 400d are embedded or hidden in the textile or fabric so that they are never in touch with the skin of the patient.

Each unit 100a, 100b, 100c, 100d, 100e, 100f includes an EMG acquisition subsystem 30a (see FIG. 5) for measuring the surface electromyography, EMG, signals of a specific muscle group of a patient.

Each EMG acquisition subsystem 30a is connected to a pair of snap-fit connectors 10a-20a, 10b-20b, 10c-20c, 10d-20d, 10e-20e, 10f-20f, for electrically and mechanically connecting the unit to a pair of electrodes (not shown) attached to the skin of a patient.

By means of the snap-fit connectors and the an EMG acquisition subsystem each unit receives, when connected to the corresponding pair of electrodes attached to the patient's body, the surface electromyography, EMG, signals of muscle group of the patient.

The muscular activity pattern recognition and feedback generation subsystem system 200 receives said surface EMG signals. These data can be stored for further analysis, or can be processed for feature extraction for its visualization. It can also be used for evaluation of bad muscular activity classification, by means of a classifying algorithm, to determine whether a correction of the current muscular activity pattern is needed.

Figure 5:
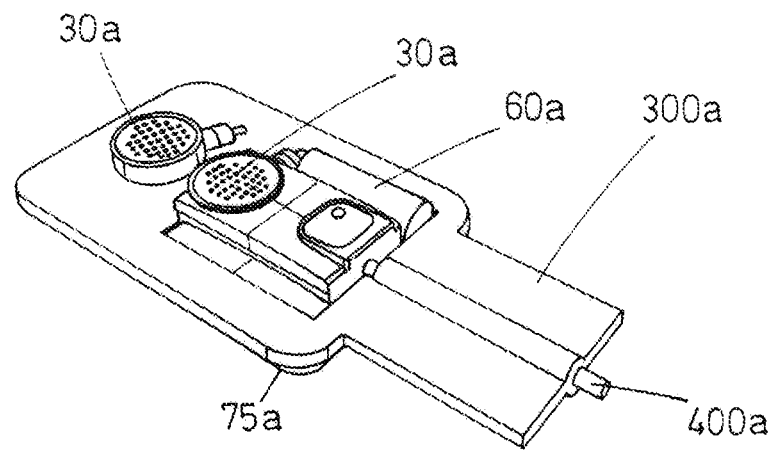
FIG. 5 shows the first unit of FIGS. 3 and 4, partially disassembled.

As shown in FIG. 5, each unit (in this case the first unit 100a is shown) also includes a vibration actuator 60a for providing haptic stimuli to the area of said muscle group of the patient. Since vibration can be transmitted by the unit itself, the vibration actuators 60a need not be in contact with the skin.

If upon analysing the surface EMG signals received from each unit the muscular activity pattern recognition and feedback generation subsystem 200 decides that feedback is needed, it activates the corresponding vibration actuator 60a.

The second unit 100b and the fifth unit 100e are attached to a central portion 300e of the belt 300 in a parallel manner.

The belt 300 has a set of four straps 300a, 300b, 300c, 300d at which ends are attached the first, third, fourth and sixth units 100a, 100c, 100d, 100e.

The straps 300a, 300b, 300c, 300d have an adjustable length and are arranged relative to each other such that, upon attaching the device 1 to a patient by connecting each pair of snap-fit connectors to each pair of electrodes:

the fourth unit 100d is set at 45° with respect to the second and fifth units 100b, 100e;

the first unit 100a is set at 135° with respect to the second and fifth units 100b, 100e;

the third unit 100c is set at −135° with respect to the second and fifth units 100b, 100e;

the sixth unit 100e is set at −45° with respect to the second and fifth units 100b, 100e.

With this specific distribution of the six units, the device of the invention is capable of:

measuring the surface EMG signals of the left side of the latissimus dorsi muscle group and to provide haptic stimuli in the area of that muscle group by means of the first unit 100a;

measuring the surface EMG signals of the left side of the erector spinae group and to provide to haptic stimuli in the area of that muscle group by means of the second unit 100b;

measuring the surface EMG signals of to the left side of the external oblique muscle group and provide to haptic stimuli in the area of that muscle group by means of the third unit 100c;

measuring the surface EMG signals of the right side of the latissimus dorsi muscle group and to provide haptic stimuli in the area of that muscle group by means of the fourth unit 100d;

measuring the surface EMG signals of the fourth side of the erector spinae group and to provide haptic stimuli in the area of that muscle group by means of the fifth unit 100e;

measuring the surface EMG signals of to the right side of the external oblique muscle group and to provide haptic stimuli in the area of that muscle group by means of the sixth unit 100f.

It is important that the device of the invention is able to measure the surface EMG signals of the latissimus dorsi, external oblique and erector spinae muscle groups, since these are the principal muscular groups responsible for the spinal cord extension, lateral bending, and pelvic rotation. They are also the principal muscle groups that are analysed in the medical assessments for low back pain patients. The applicant has been able to conclude, after performing numerous tests regarding the activity of different muscle groups, that the synergies between muscles are minimum for those muscle groups by performing a principal component analysis (Miljkovic N. et al, "*Independent component analysis of EMG for posture detection: sensitivity to variation of posture properties*". 19th Telecommunications Forum, TELFOR 2011, 22-24 Nov. 2011, Belgrade, Serbia. IEEE Press, 2011. p. 47-50, Article No. 6143889).

Therefore, the device provided by the invention is a wearable device, such as a belt, that monitors the muscle pattern of low-back muscles using surface EMG. And, if it detects some incorrect pattern, such as an asymmetric or over-activated pattern, it provides feedback stimuli to the user that corrects the pattern.

Both the processing and decision of whether a posture is correct is based on the comparison with the surface EMG signals of the user with their own signals (e.g. asymmetry, co-contraction, and contractions kept for too long), so that huge databases of surface EMG signals as in the prior art is not needed.

Figure 2:
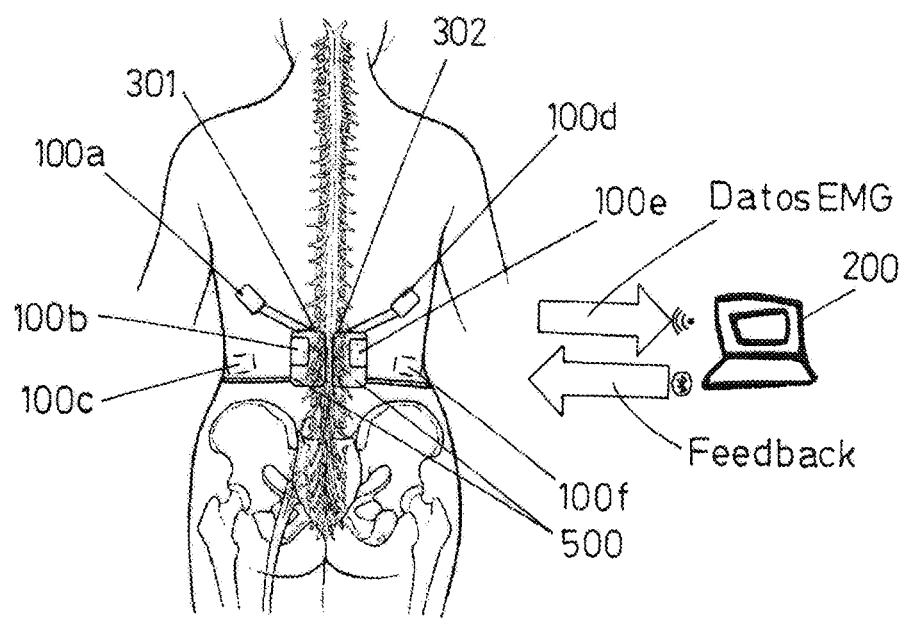
FIG. 2 shows a second preferred embodiment of the device, worn on the body of a patient.

In the embodiment shown in FIG. 2, the device comprises the six units 100a, 100b, 100c, 100d, 100e, 100f attached to a belt made of a textile or fabric, which is made of two symmetric portions 301 and 302. In this embodiment of the device the muscular activity pattern recognition and feedback generation subsystem is not attached to the belt, but it is a separate item, such as a personal computer 200, a tablet, a smartphone or a specifically designed printed circuit board.

In order to enable communication between the six units and the computer 200, the device further comprises a remote control unit 500, RCU, also attached to the belt. As shown in FIG. 2, data relative to EMG signals flows from the RCU 500 to the computer 200; and once the computer has processed the EMG data it provides feedback data for activating the corresponding vibrations actuators 60a.

Figure 3:
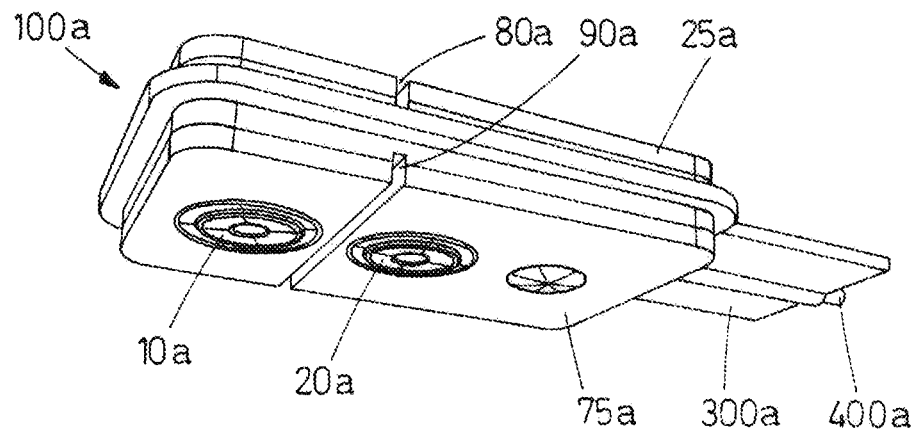
FIG. 3 shows a lower perspective view of one of the units of the device.
Figure 4:
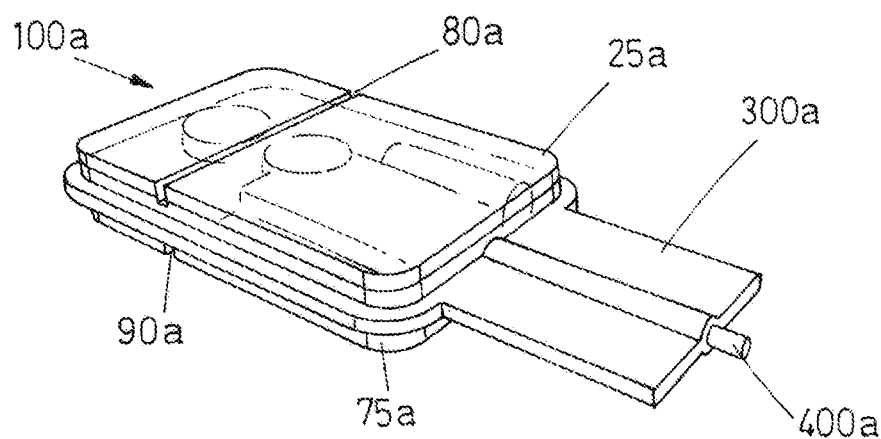
FIG. 4 shows an upper perspective view of the first unit of FIG. 3.

As shown in FIGS. 3 and 4, each unit 100a comprises a casing with an upper portion 25a and a lower portion 75a. The upper and lower portions 25a, 75a enclose the end of the first strap 300a. The third, fourth and sixth units 100c, 100d, 100f are arranged in a similar way at the end of the second, third and fourth straps 300b, 300c and 300d.

Upper portion 25a and lower portion 75a of the unit casing are each provided with a slot 80a, 90a which allow the casing to slightly bend for a better adaption to the skin of the patient.

FIG. 5 shows the first unit 100a, in which the upper portion 25a of the casing has been removed, for better showing the components inside each unit. As it can be seen, each unit includes the EMG data acquisition subsystem 30a and the vibration actuator 60a.

FIG. 6 shows the lower portion 75a of the casing which is provided with a couple of holes 50a, each hole being dimensioned to hold one snap-fit connector, so that each connector is exposed through the casing and it slightly protrudes from the surface of the casing.

Surface EMG signals as captured by each pair of electrodes by means of the connectors usually have low amplitude (in the order of 10 μV) and need to be conditioned and/or digitalized (sampled) before being sent to the muscular activity pattern recognition and feedback generation subsystem. The device also comprises an electronic system intended to amplify, band-pass filter, normalize and/or sample EMG signals. These electronic systems are essentially known in the art and therefore, are not described in more detail.

The muscular activity pattern recognition and feedback generation subsystem takes decisions depending on the working status of the overall system. When the system is being used for therapy, it requests the user to perform certain exercises. Each exercise has its own activity pattern. When this pattern is not reached, it provides a feedback.

While the system is being used in the wrong pattern recognition mode, the decision algorithm is a classifying algorithm that monitors parameters calculated from the processed EMG signals, and decides whether the current muscular activation pattern is acceptable. This classifying algorithm can be implemented using three different approaches:

1) Threshold approach: the physiological and normal values of the decision parameters are known from medical literature. The algorithm checks in real time whether the values of the parameters are within their respective acceptable margins. For example, the normal asymmetry between the levels of activation of the left and right sides of the back is of up to 5%; values above that are considered not acceptable. On the other hand, the activity of the muscles can be very symmetric, but over-activated (co-contraction), which can also be detected by analysing those parameters.

2) Pattern recognition: from a given number of selectable or classifiable postures or gestures, a pattern is generated by with their corresponding signals and the features extracted from them. The classifier determines whether the input signal corresponds to one of the classifiable postures or gestures. The algorithm identifies specific signal features which correspond to the given postures or gestures. Identification of useful signal patterns is facilitated with different discriminatory analysis techniques which compare the actual signal and the extracted features to patterns which correspond to given postures and gestures.

3) Machine learning: algorithms such as artificial neural networks (e.g. perceptrons or based on Learning Vector Quantization) or statistical classification. These algorithms can automatically learn in a supervised way, by providing them with examples of postures and gestures the system can classify.

In addition, based on the detected muscular activity history of the user, the algorithm also updates itself using automatic learning techniques such as Bayesian inference. That is, as the user learns to correct their posture, the algorithm becomes more "demanding" by lowering its acceptance values.

The device 1 of the invention, with its distributed design with all its elements kept together by the belt 300, can be advantageously made very thin, so that performing any exercise is feasible, even in a supine position.

In this text, the term "comprises" and its derivations (such as "comprising", etc.) should not be understood in an excluding sense, that is, these terms should not be interpreted as excluding the possibility that what is described and defined may include further elements, steps, etc.

In the context of the present invention, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially".

The invention claimed is:

1. A device (1) for the assessment, prevention and treatment of low back pain, comprising:
    first, second, third, fourth, fifth and sixth units (100a, 100b, 100c, 100d, 100e, 100f, each unit comprising:
        an EMG acquisition subsystem (30a) for measuring surface electromyography, EMG, signals of a specific muscle group of a patient provided by a pair of electrodes configured to be attached to skin of the patient;
        connecting means (10a-20a, 10b-20b, 10c-20c, 10d-20d, 10e-20e, 10f-20f) for connecting the EMG acquisition subsystem (30a) to the pair of electrodes so that each unit receives the surface electromyography, EMG, signals of a specific muscle group of the patient;
        an actuator (60a) for providing haptic stimulus to the specific muscle group of the patient;
        the device further comprising: an electronic system adapted to capture, amplify, filter and send the surface EMG signals; at least one muscular activity pattern recognition and feedback subsystem (200, 500) configured for extracting certain features of the surface EMG signals;
        extracting certain features of the surface EMG signals;
        interpreting the surface EMG signals and determining a muscular activity pattern based on the extracted features;
    determining whether a correction of the muscular activity pattern is needed;
        if correction is needed, activating the actuators (60a); and
        a wearable garment (300, 301, 302) comprising:
        a central portion (300e) to which the second and fifth units (100b, 100e) are attached parallel to each other;
        a set of four straps (300a, 300b, 300c, 300d) to which the first, third, fourth and sixth units (100a, 100c, 100d, 100f) are attached, the straps having an adjustable length and being arranged relative to each other so that, upon connecting the device to each pair of electrodes:
        the fourth unit (100d) is set at a position between 40° and 50° with respect to the second and fifth units (100b, 100e);
        the first unit (100a) is set at a position between 130° and 140° with respect to the second and fifth units (100b, 100e);
        the third unit (100c) is set at a position between −130° and −140° with respect to the second and fifth units (100b, 100e);
        the sixth unit (100e) is set at a position between −40° and −50° with respect to the second and fifth units (100b, 100e).

2. The device (1) according to claim 1, wherein the muscular activity pattern recognition and feedback generation subsystem (200) uses a classifying algorithm based on threshold approach, and/or on pattern recognition, and/or on machine learning for deciding whether a correction of the current muscular activity pattern is needed.

3. The device (1) according to claim 1, wherein the haptic stimulus provided by the actuators (60a) is mono-modal or multimodal.

4. The device (1) according to claim 1, wherein the haptic stimulus provided by the actuators (60a) is one or more of:

skin stretching, temperature change, vibration, simple touch, pinching of skin hair and electrical stimulation.

5. The device (1) according to claim 1, wherein the muscular activity pattern recognition and feedback generation subsystem (200) is also attached to the wearable garment (300).

6. The device (1) according to claim 1, where in the device further comprises a remote control unit (500) attached to the wearable garment (300) for enabling communication between the units (100*a*, 100*b*, 100*c*, 100*d*, 100*e*, 100*f*) and the muscular activity pattern recognition and feedback generation subsystem (200).

7. The device (1) according to claim 1, wherein the wearable garment is a one-piece item (300).

8. The device (1) according to claim 1, wherein the wearable garment is a multiple-piece item (301, 302).

9. The device (1) according to claim 1, which further comprises the electronic system adapted to band-pass filter, normalize and/or sample the surface EMG signals.

* * * * *